United States Patent
Dunn et al.

(10) Patent No.: US 6,796,317 B2
(45) Date of Patent: Sep. 28, 2004

(54) LIQUID WASTE DISPOSAL CANISTER

(75) Inventors: James L. Dunn, Topeka, KS (US); Lawrence E. Guerra, Overland Park, KS (US)

(73) Assignee: Dornoch Medical Systems, Inc., Riverside, MO (US)

( * ) Notice: Subject to any disclaimer, the term of this patent is extended or adjusted under 35 U.S.C. 154(b) by 0 days.

(21) Appl. No.: 10/382,365

(22) Filed: Mar. 6, 2003

(65) Prior Publication Data

US 2003/0164180 A1 Sep. 4, 2003

Related U.S. Application Data

(60) Division of application No. 09/870,215, filed on May 30, 2001, now Pat. No. 6,588,436, which is a continuation-in-part of application No. 09/483,295, filed on Jan. 14, 2000, now Pat. No. 6,263,887.

(51) Int. Cl.[7] .................................................. B08B 3/00
(52) U.S. Cl. ........................ 134/116; 134/135; 422/303
(58) Field of Search .............................. 134/116, 104.2, 134/135, 150, 166 R, 167 R, 168 R, 177, 186; 422/302, 303

(56) References Cited

U.S. PATENT DOCUMENTS

| | | | | |
|---|---|---|---|---|
| 4,653,518 A | * | 3/1987 | Adachi | 134/62 |
| 5,776,260 A | * | 7/1998 | Dunn et al. | 134/18 |
| 5,807,359 A | * | 9/1998 | Bemis et al. | 604/322 |
| 5,871,476 A | * | 2/1999 | Hand | 604/317 |
| 5,901,717 A | * | 5/1999 | Dunn et al. | 134/56 R |
| 5,960,837 A | * | 10/1999 | Cude | 141/65 |
| 5,975,096 A | * | 11/1999 | Dunn et al. | 134/56 R |

* cited by examiner

Primary Examiner—Frankie L. Stinson
Assistant Examiner—Joseph Perrin
(74) Attorney, Agent, or Firm—Piper Rudnick LLP

(57) ABSTRACT

A canister for use in a liquid disposal device featuring a lid removal bracket and a canister bracket. The canister includes a lid featuring a patient port, a vacuum port and a lip adapted to be engaged by the lid removal bracket of the liquid waste disposal device. The canister also includes a body including an open top surrounded by a circumferential rim that is engaged by the lid in a removable fashion. A tab is attached to an exterior surface of the body of the canister in a generally horizontal extending fashion and is sized and vertically spaced from the circumferential rim so as to engage the canister bracket of the liquid waste disposal device when the canister body is positioned therein and turned about a generally vertical axis.

6 Claims, 8 Drawing Sheets

LIQUID WASTE DISPOSAL CANISTER

CROSS REFERENCE TO RELATED APPLICATIONS

This application is a divisional application of U.S. patent application Ser. No. 09/870,215 filed May 30, 2001, now U.S. Pat. No. 6,588,436, which is a continuation-in-part of U.S. patent application Ser. No. 09/483,295 filed Jan. 14, 2000, and issued on Jul. 24, 2001, as U.S. Pat. No. 6,263,887.

BACKGROUND OF THE INVENTION

I. Field of the Invention

The present invention relates generally to liquid waste disposal and canister flushing, and in particular to the disposal of liquid medical waste from containers which are flushed and cleaned to permit reuse.

II. Description of the Related Art

Various forms of liquid waste are commonly encountered in a variety of different situations. For example, liquid medical wastes are commonly produced in surgery and other medical procedures. Such wastes can include blood and other body fluids of patients, and major surgery can produce a number of containers of such waste from a single patient. Liquid medical waste generates significant disposal problems due to its possible contamination with various infectious diseases, including AIDS, hepatitis, MRSA and tuberculosis. In an effort to combat the risks associated with handling such liquid medical wastes and to protect medical personnel from the spread of infectious diseases, disposal procedures have become increasingly complicated and expensive.

One type of disposal procedure for liquid medical wastes involves emptying the waste canisters from surgery into specially designed plumbing fixtures. However, this procedure can involve risks associated with splash back and aerosolization whereby medical personnel can be exposed to the waste and bacteria present therein.

Another type of procedure involves the centralized collection of the waste with specially designed equipment having a liquid waste reservoir that must periodically be dumped. Such equipment is generally relatively expensive and can add significantly to the cost of equipping a hospital operating room or other treatment facility.

Yet another method of disposing of liquid medical waste involves mixing it with a solidifying agent in the container. The medical waste in the container is then disposed of pursuant to regulations governing the disposal of bio-hazardous waste. The disadvantages with this disposal method include the cost of the canister, which becomes a single-use item, and the extra charges for disposing of bio-hazardous waste, which is sometimes referred to as "red bag" waste.

Liquid medical waste disposal procedures can come under rules and regulations imposed by various governmental and regulatory agencies, including the Occupational Safety and Health Administration (OSHA), the Food and Drug Administration (FDA), the Center for Disease Control (CDC) and the Department of Transportation (DOT).

Heretofore there has not been available a liquid medical waste disposal system and method with the advantages and features of the present invention.

SUMMARY OF THE INVENTION

A liquid waste disposal and canister flushing system for a canister having a press fit lid features a cabinet having an opening with a hinged lid. A sink is positioned within the cabinet and communicates with a drain. A mounting bracket is affixed to the cabinet and includes a motor, a shaft connected to a canister bracket, and a shaft connected to a lid removal bracket. A canister sealed with a press fit canister lid is positioned in the canister bracket. As the canister is secured to the canister bracket the lid is loosened and positioned on a lid removal bracket. The cabinet is then closed. The canister is automatically rotated by the canister bracket to an inverted position within the chamber so that the contents drain out of the canister. The canister lid is rotated, relative to the canister, by the lid removal bracket to a position displaced from the canister and released so that it falls into a disposal collection tray. A pressurized cleaning solution and water are activated and sprayed within the chamber so that the canister is flushed and its contents drain into the sink and down the drain. Once the canister is sanitized it may be removed from the system and reused.

OBJECTS AND ADVANTAGES OF THE INVENTION

The principal objects and advantages of the present invention include: providing a liquid waste disposal and canister flushing system; providing such a system which facilitates the relatively inexpensive disposal of medical waste; providing such a system which permits safe reuse of medical waste containers; providing such a system which is relatively easily adapted for use with existing medical waste containers; providing such a system which reduces the splashing of medical waste being disposed; providing such a system which can reduce the hazards associated with handling and disposing of medical waste; providing such a system which facilitates the discharge of medical waste into a sewer system; providing such a system which can reduce the amount of disposable components associated with medical waste disposal; providing such a system which provides effective neutralization of various bacteria and infection sources; providing such a system which is usable by medical personnel with relatively little training; providing such a system with a control system which is at least partially automated; providing such a system which is relatively portable; providing such a system which is relatively compact; providing such a system which can be installed with relatively simple plumbing and electrical connections; providing such a system which is economical to manufacture and use, efficient in operation, capable of a long operating life and generally well adapted for the proposed usage thereof; providing a liquid medical waste disposal and canister flushing method; providing such a method which is relatively efficient; providing such a method which is relatively safe; providing such a method which is relatively economical and providing such a method which is particularly well adapted for the proposed usage thereof.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

DETAILED DESCRIPTION OF THE INVENTION

Figure 1:
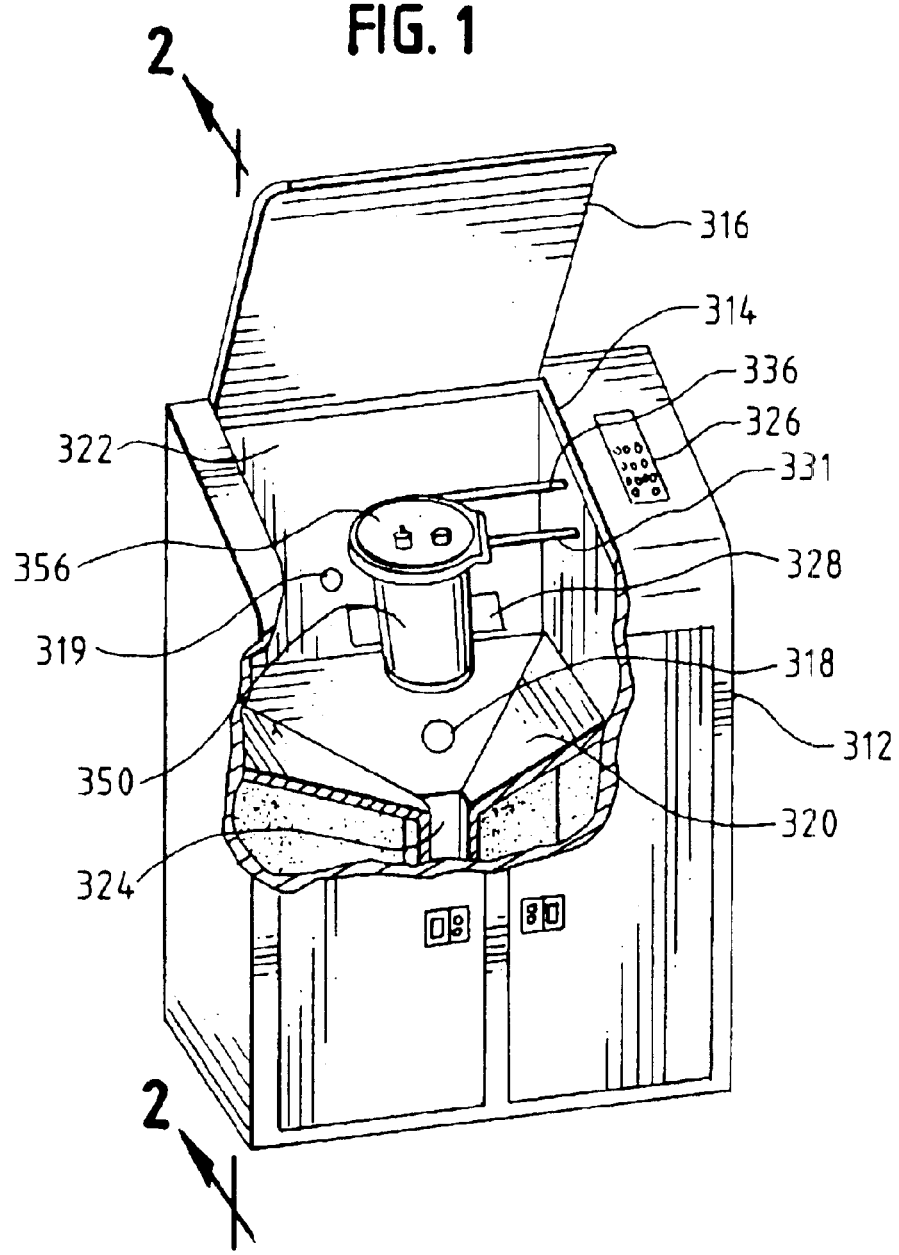
FIG. 1 is a partially broken-away frontal perspective view of an embodiment of the liquid medical waste disposal and canister flushing system of the present invention.
Figure 2:
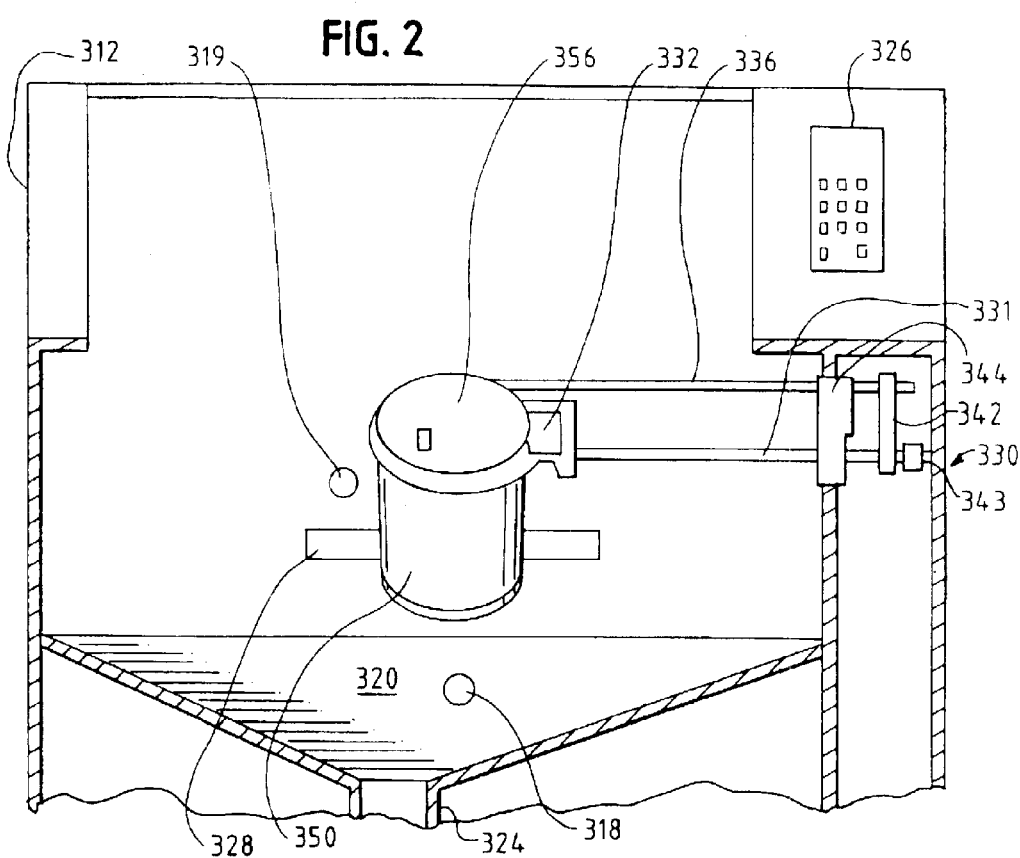
FIG. 2 is a fragmented front sectional view of the liquid medical waste disposal and canister flushing system of FIG. 1 taken along line 2—2.

A preferred embodiment of the system of the present invention is indicated in FIGS. 1 and 2. A cabinet 312 features an opening 314 that may be covered by a hinged lid 316. A sink 320 is formed within the cabinet so that a chamber 322, which may be accessed through opening 314, is defined. The sink communicates with a drain 324 which leads to a plumbing system so that waste disposed in the sink is carried out of the hospital. As described in commonly-assigned U.S. Pat. No. 5,901,717, drain 324 may optionally communicate with a holding tank for treating the waste before it leaves the hospital. A control panel 326 is positioned upon the cabinet for ease of access by the system operator.

A canister rotation mechanism 330 is affixed to the cabinet 312 as best seen in FIG. 2. The canister 350 is supported by a rotatable device such as a canister bracket 332 and the press fit canister lid 356 is supported by the lid removal bracket 338 of the canister rotation mechanism 330. A disposal collection tray 328 is affixed to the cabinet 312. The disposal collection tray 328 is positioned above the sink 320 and under the rotated position of the lid removal bracket 338 so that it receives the canister lid 356 after it falls from the lid removal bracket 338.

Figure 3:
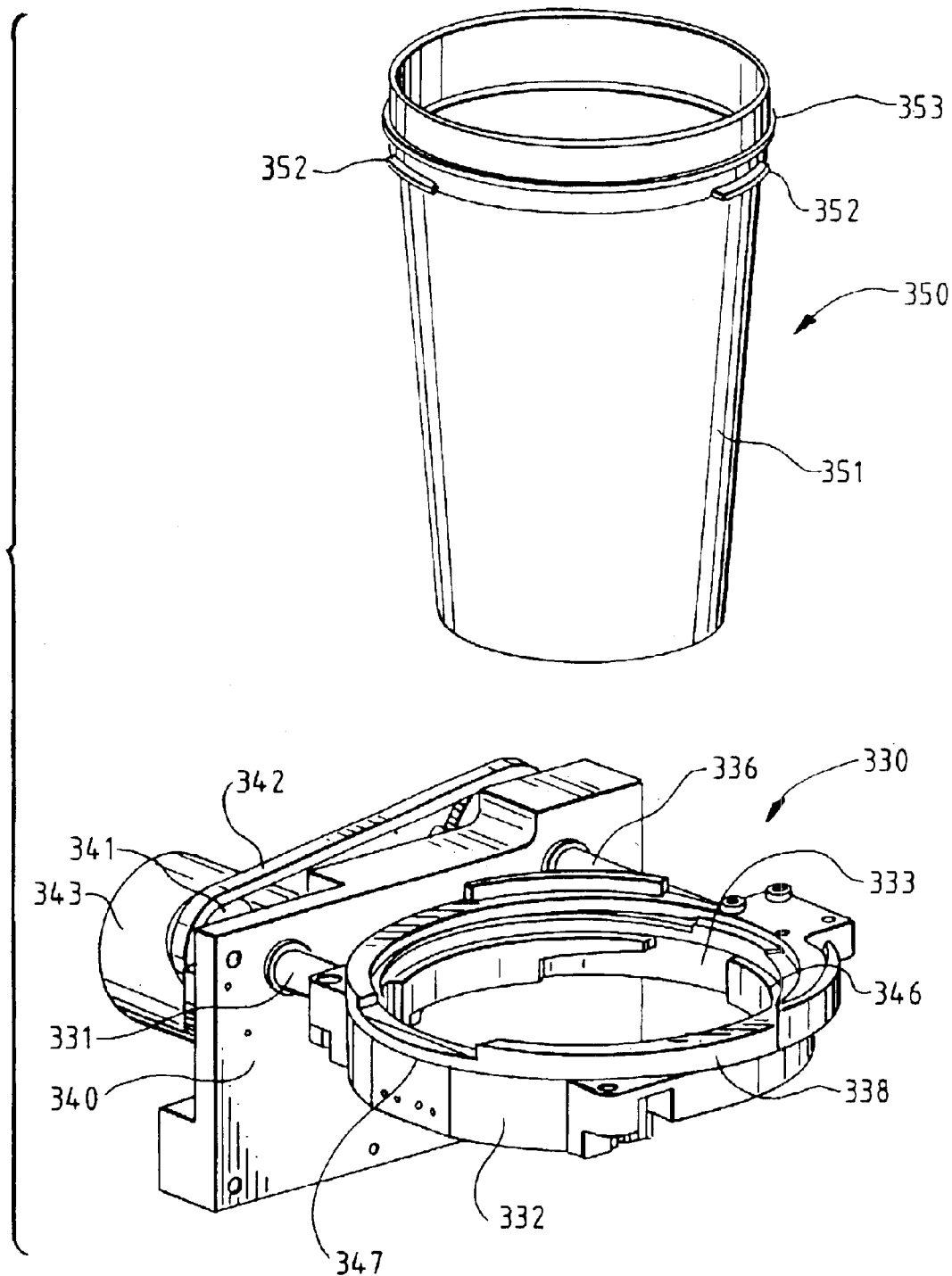
FIG. 3 is a perspective view of the canister bracket and the lid removal bracket.

The canister rotation mechanism for use in the system of FIG. 1 is indicated in general at 330 in FIG. 3. The canister rotation mechanism 330 is connected to the cabinet 312 by a mounting bracket 340. The rotation mechanism 330 includes the mounting bracket 340, a motor 343, pulleys 341, timing belts 342, a shaft 331 connected to a canister bracket 332, and a shaft 336 connected to a lid removal bracket 338. The shafts 331 and 336 are motorized and are connected via pulleys and timing belts such that the shafts simultaneously rotate the canister bracket 332 containing canister 350 and the lid removal bracket 338 holding canister lid 356 (shown in FIG. 7) in the same direction, e.g., clockwise. Alternative mechanisms, may be used to rotate the brackets, the canister and the canister lid such as a chain and sprocket, gears, or bearings, and the canister bracket may be rotated either before or after the lid removal bracket is rotated.

The canister 350 is also illustrated in FIG. 3. The canister 350 includes a body portion 351 with a truncated, generally frustoconical shape. The canister 350 has an open top with three, equally spaced, horizontally extending tabs 352 that are positioned approximately one inch from the top of the canister 350. The canister 350 also has a circumferential rim 353. The canister may be molded from polycarbonate plastic, which is reusable and autoclavable up to 220° F., or other materials such as Radel plastic, which is autoclavable up to 321° F.

Figure 4A:
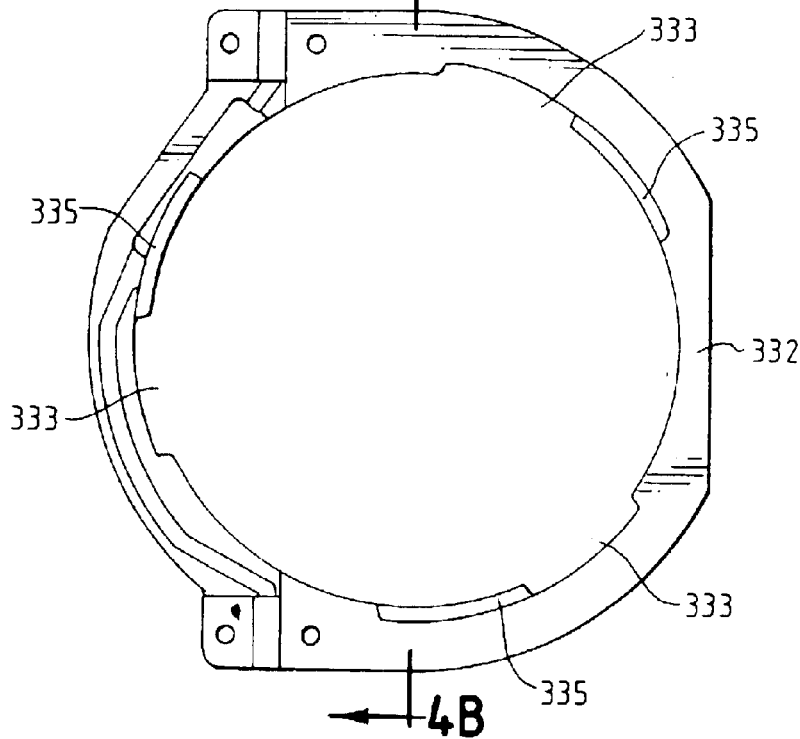
FIG. 4A is a bottom view of the canister bracket.
Figure 4B:
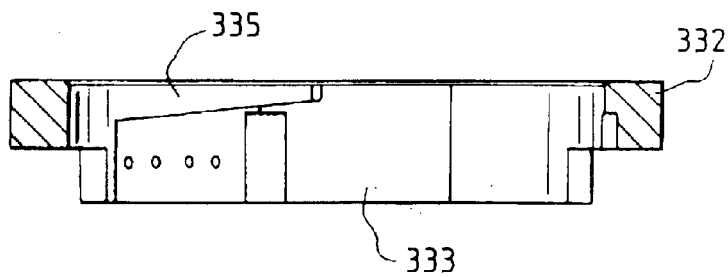
FIG. 4B is a sectional view of the canister bracket of FIG. 4A taken along line 4B—4B.

The canister bracket 332 is circular with an inner edge 346 and outer edge 347. Also, as illustrated in FIG. 4A, the canister bracket 332 includes three notches 333 cut out of the inner edge 346 with slight ramp surfaces 335 positioned along the underside adjacent to the notches 333. FIG. 4B is a sectional view of the canister bracket 332 taken along line 4B—4B. FIG. 4B illustrates a slight ramp surface 335 adjacent to a notch 333 of the canister bracket 332.

As seen in FIG. 3, the bottom surface of the lid removal bracket 338 is located above the canister bracket 332. The canister lid 356 (FIG. 6) includes a circumferential lip 357 which rests on the lower rim 349 (FIG. 5) of the lid removal bracket 338 when the canister 350 is placed in the rotation mechanism.

Figure 5:
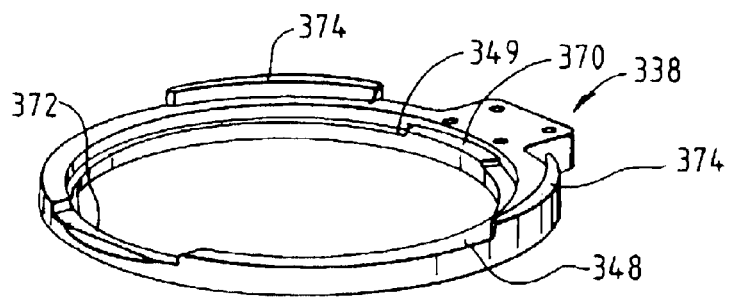
FIG. 5 is a perspective view of the lid removal bracket.

FIG. 5 illustrates the details of the circular lid removal bracket 338. An upper rim 348 and a lower rim 349 form the top surface. The lower rim 349 includes a slightly elevated portion 370 towards the back of the lid removal bracket 338. The slightly elevated portion 370 assists in the removal of the canister lid when the canister is positioned in the canister bracket 332 and lid removal bracket 338. The lower rim 349 also includes an indentation 372 in the front of the lid removal bracket 338. The indentation 372 provides a guide for the canister when it is inserted into the canister bracket 332. More specifically, one of the canister tabs, illustrated at 352 in FIG. 3, must be oriented to pass through the indentation 372 of the lid removal bracket 338 and the notch 333 (FIG. 4A) of the canister bracket 332 when the canister 350 is inserted in the cabinet 312 (FIG. 1). The lid removal bracket 338 also includes two upright projections 374 positioned on the upper rim 348 towards the back of the lid removal bracket 338. The upright projections 374 direct the removed canister lid 356 when the lid removal bracket 338 rotates.

Figure 6:
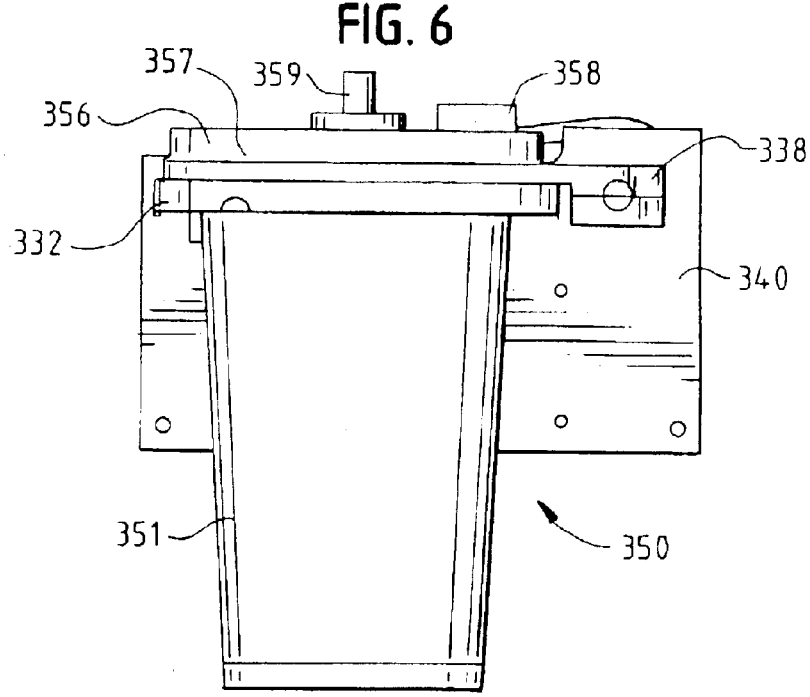
FIG. 6 is a side view of the rotate bracket and the canister in their initial position with the canister lid attached to the canister.
Figure 7:
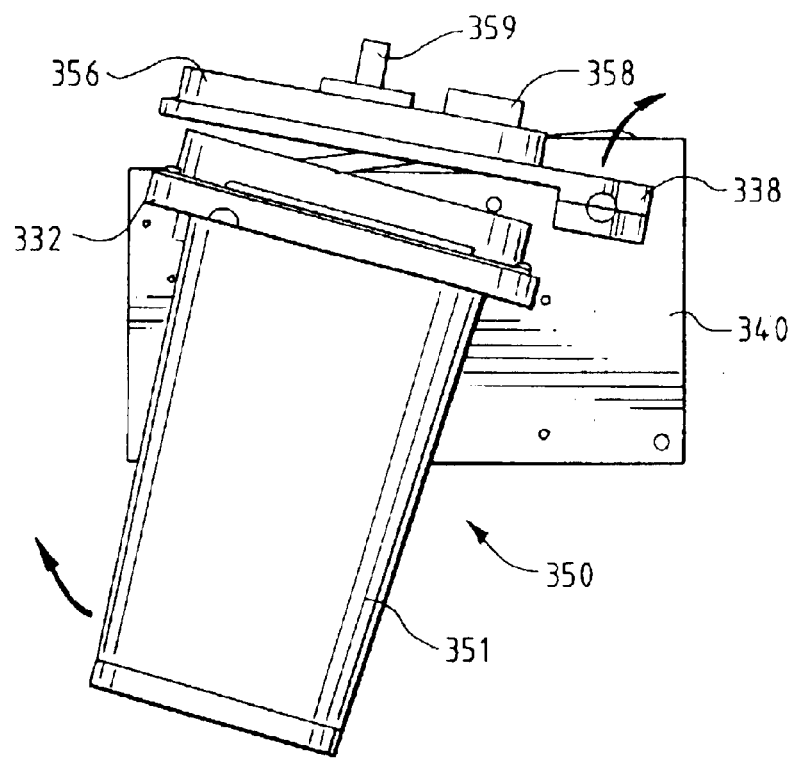
FIG. 7 is a side view of the canister bracket and the canister in a rotated position and with the canister lid supported by the removal bracket.

FIGS. 6 and 7 illustrate the canister lid 356 which includes a patient port 358 and a vacuum port 359 integrally molded onto the top surface of the canister lid 356. The canister lid 356 is removably secured to the canister 350 in a press-fit fashion and has a lip larger than the rim of the canister 350. The canister lid may be molded from, for example, polystyrene plastic.

As previously described in FIG. 5, the lid removal bracket 338 is a circular bracket. It includes an upper rim 348 and a lower rim 349. The lower rim 349 allows the lower surface of the circumferential lip of the canister lid 356 to rest there when the canister 350 is positioned in the canister bracket 332. The lid removal bracket 338 rotates in the same direction as the canister bracket 332 to a point where the lid 356 will fall off the lid removal bracket 338 into the disposal collection tray 328 (see FIGS. 8 and 9).

Once the material in the canister 350 is ready to be disposed of, the canister 350 is positioned within the canister bracket 332 with its three horizontally extending tabs 352 passing through the three notches 333 on the canister bracket 332. (See FIG. 6) When the canister 350 with the lid 356 attached, is placed in the canister bracket 332, the circumferential lip of the canister lid 356 rests on the lower rim 349 of the lid removal bracket 338. The operator rotates the canister 350 about a vertical axis approximately 10 to 30 degrees counter clockwise so that the three horizontally extending canister tabs 352 travel along the ramp surfaces 335 of the canister bracket 332 until the horizontally extending canister tabs 352 are secured underneath the canister bracket 332. As the canister 350 is turned it is forced downwardly away from the canister lid 356 as the lower rim 349 of the lid removal bracket 338, including the slightly elevated portion 370, pushes upwardly relative to the canister 350, thereby loosening the attachment between the canister 350 and the canister lid 356. The canister lid 356 is not removed by this action it is merely loosened. FIG. 6 illustrates an initial position of the canister 350 secured to the canister bracket 332 with the tabs 352 rotated in a locked position.

Figure 8:
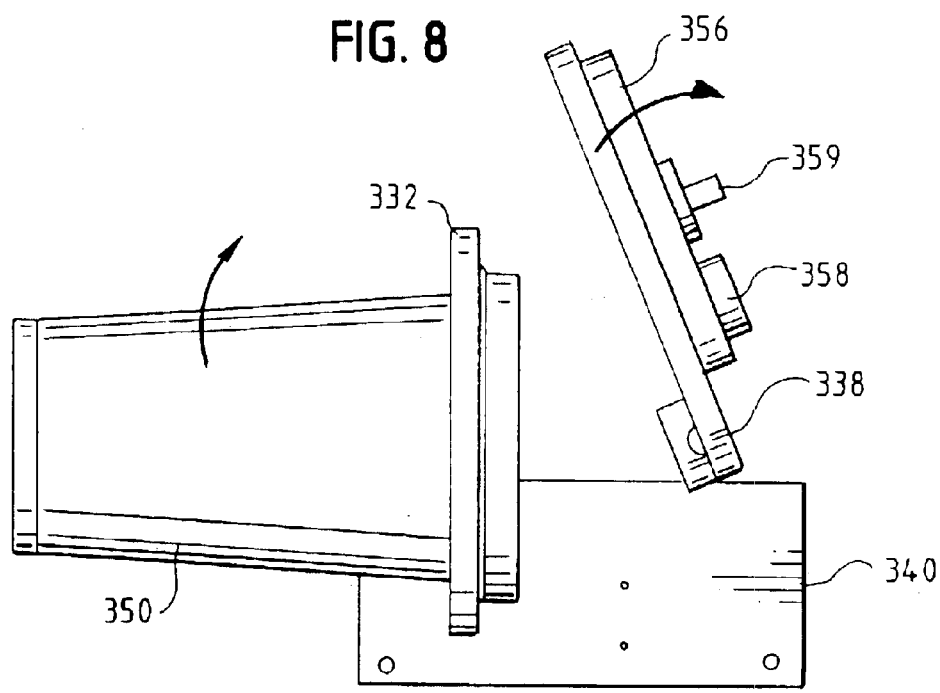
FIG. 8 is a side view of the canister bracket and the canister in a 90 degree rotated position and the canister lid supported by the removal bracket.
Figure 9:
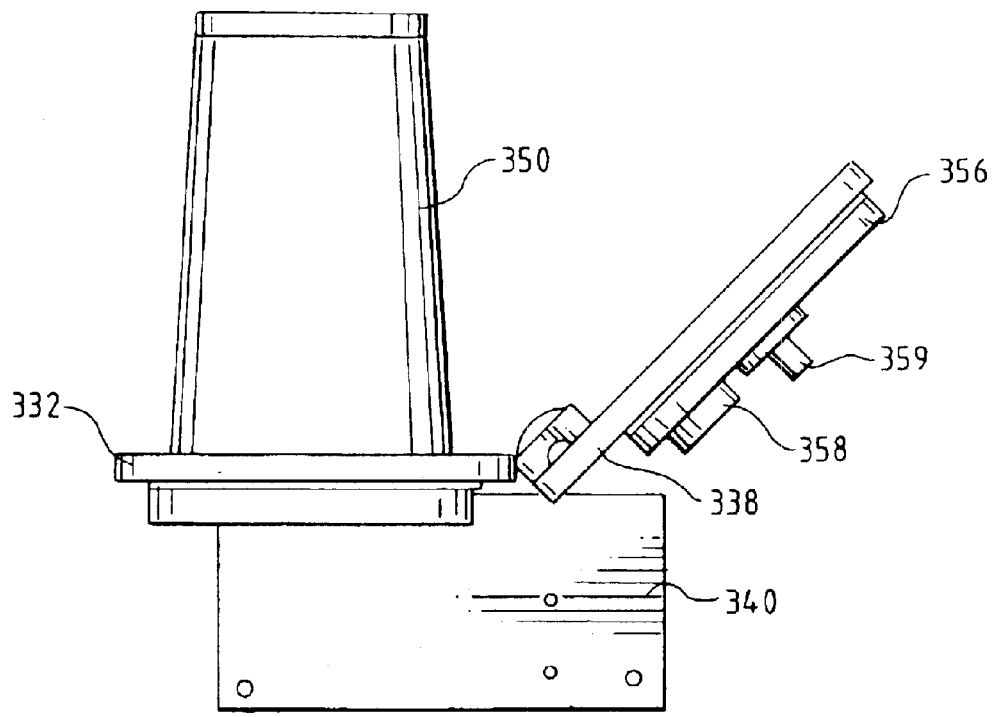
FIG. 9 is a side view of the canister bracket and the canister in a rotated position for drainage and the lid removal bracket in a further rotated position where by the canister lid is positioned to fall off the removal bracket.

As seen in FIGS. 7–9, the canister bracket 332 and the lid removal bracket 338 rotate the canister 350 in the same direction but from different locations thereby forcing the canister lid 356 from the canister 350 and rotating the canister 350 to a drainage position. Once the canister 350 is rotated 90 degrees, as illustrated in FIG. 8, the canister lid 356 is completely removed from the canister 350 and supported by the lid removal bracket 338. As illustrated in FIG. 9, the canister bracket 332 and lid removal bracket 338 continue to rotate until the canister 350 is rotated 180 degrees from the initial position and the canister lid 356 is positioned to drop by gravity, guided by upright projections 374, into the disposal collection tray 328 positioned above the sink 320. As the canister 350 is rotated, its contents empty into the sink 320.

A spray system located within the sink and housing next applies a cleaning solution to the canister 350. As illustrated in FIG. 2, the spray system includes a telescoping nozzle 318 and a rotating nozzle 319. The telescoping nozzle 318 is positioned in the bottom of the sink 320. The telescoping nozzle 318 extends up into the inverted canister 350 once the flushing cycle is activated. A solution is sprayed out of the telescoping nozzle 318 to clean the inside of the canister 350. Rotating nozzle 319 is positioned near the back of the sink 320. The rotating nozzle 319 sprays the solution on the outside of the canister 350 thereby cleaning the outside of the canister 350. Once the spray system has cleaned the canister 350, the canister 350 is rotated back to its initial position and it is ready for removal.

Figure 10A:
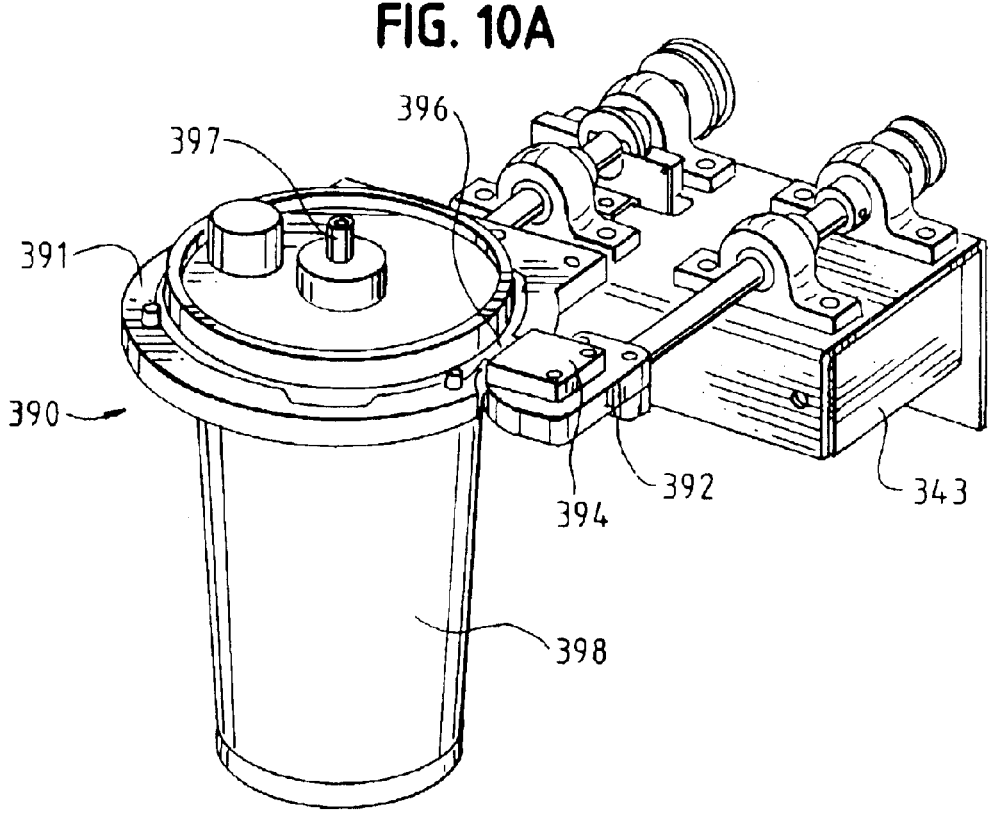
FIG. 10A is a perspective view of an alternative embodiment of the rotating mechanism with the canister rotation mechanism including a removal bracket combined with a lid grip to remove the canister lid from the canister.
Figure 10B:
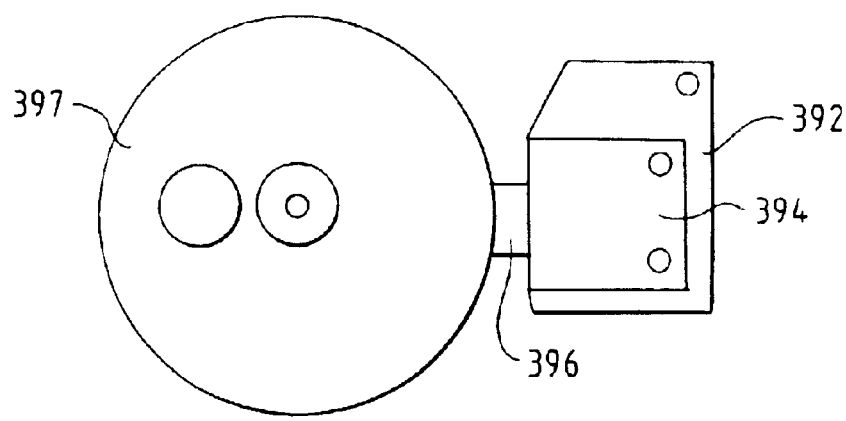
FIG. 10B is an enlarged top view of the lid gripping mechanism for the removal bracket.

An alternative canister rotating mechanism is illustrated in general at 390 in FIG. 10A. The rotating mechanism of FIG. 10A is similar to FIG. 3 except, that the removal bracket 392 includes a lid grip 394. The canister lid 397, in the alternative embodiment, includes a horizontal lid removal tab 396. The lid removal tab 396 is molded with the canister lid 397 and extends in a radial direction from the edge of the canister lid 397. As the canister 398 is turned into its locked position, upon insertion, the horizontal lid removal tab 396 slides in the lid grip 394. As illustrated in FIG. 10B, the lid removal bracket 392 supports the lid grip 394 as the lid grip 394 clamps the lid removal tab 396. The lid grip 394 clamps the lid removal tab 396 such that the lid grip 394 is connected to the bottom of the lid removal tab 396 near the inner edge of the lid removal tab 396 next to the canister lid 397 and the lid grip 394 is connected to the top of the lid removal tab 396 near the outer edge of the lid removal tab 396. As the lid removal bracket 392 rotates, the lid grip 394 rotates until the canister lid 397 is no longer held in position by the lid grip 394. Thus, the canister lid 397 falls into a disposal collection tray.

Operation

During a surgical procedure, a tube is connected between the vacuum port 359 and a vacuum source. A second tube is connected to the patient port 358 at one end while the other end is utilized by the surgeon or nurse to withdraw blood and fluids from the patient. When the surgical procedure is completed, or the canister is full, the tubing is disconnected from the vacuum and patient ports. The vacuum and patient ports are then capped so that the canister may be transported to and inserted in the rotating bracket mounted in the cabinet 312.

With the canister secured within the canister bracket the cabinet lid 316 (FIG. 1) may be closed. This allows the drainage and flushing cycles to commence when the operator pushes a "start" button on the control panel 326. When the "start" button is pushed the rotating mechanism rotates the canister from the initial position illustrated in FIG. 6 to the drainage position illustrated in FIG. 9, and the canister lid is rotated simultaneously from the initial position illustrated in FIG. 6 to the removal position illustrated in FIG. 9. Alternatively, closing the cabinet lid may automatically activate the rotating mechanism so that the canister is rotated into the drainage position and the canister lid is rotated to the removal position. Either way blood and other fluids drain out of the canister into the sink 320 and down drain 324.

A timed delay of the commencement of the flush cycle is provided after the canister is rotated into the drainage position. This delay permits substantially complete drainage of the liquid from the canister before the flush cycle commences. This delay may be accomplished through either an automated control system or manually via separate buttons for rotating the canister and commencing the flushing cycle. In the case of the latter, the operator may merely wait for the canister to drain before pushing the button to commence the flushing cycle.

Commencement of the flushing cycle causes the pressurized cleaning solution to enter the canisters via the spray systems that is positioned in the cabinet. The cleaning solution strikes the now inverted inside bottom of the canister. As a result, the contents remaining in the canister after drainage are disinfected and flushed down the drain 324.

As a general guideline, it is desirable to flush the canister with a volume of solution equal to approximately 3 to 4 times its capacity. The cleaning solution mixture preferably comprises water and a suitable agent for killing virus and bacteria. For example, sodium hypochlorite (i.e., bleach) in a solution of about 1200 to 1400 parts per million with water has generally been found to be suitable. A delay of approximately 8 seconds has been found to be sufficient to drain the canister, and a flush cycle of approximately 45 seconds has generally been found to be sufficient.

Upon completion of the flushing cycle, the flow of diluted cleaning solution is stopped and the canister is rotated back to the initial position as illustrated in FIG. 6. The canister lid may then be removed from the disposal collection tray and the canister may be removed from the rotating bracket by turning it clockwise to position the horizontally extending tabs in the notches. The operator can then lift the canister 350 from the canister bracket 332 and out of the cabinet. The canister lid may then be disposed of and the canister itself may be reused, if desired, at a fraction of the cost of disposing of complete canisters full of medical waste.

The solution mixture is preferably chosen to meet the particular objectives of a disposal and flushing system. For example, disinfection and flushing are generally the primary objectives with liquid medical waste containers, which for most reuse purposes do not have to be cleaned to the point where they would be considered sterile, since sterility is normally not required for liquid medical waste canisters. The lid would generally be considered "white" trash in medical facilities due to relatively low concentrations of liquid medical waste thereon and thus would not be subjected to the more stringent requirements typically in place for handling and disposing of the actual liquid medical wastes.

The flushed liquid medical waste from drain 324 mixes with the effluent from the medical facility in its plumbing drainage system and is normally discharged into a municipal sewer system at levels well below the maximums permitted for medical waste effluents.

Figure 11:
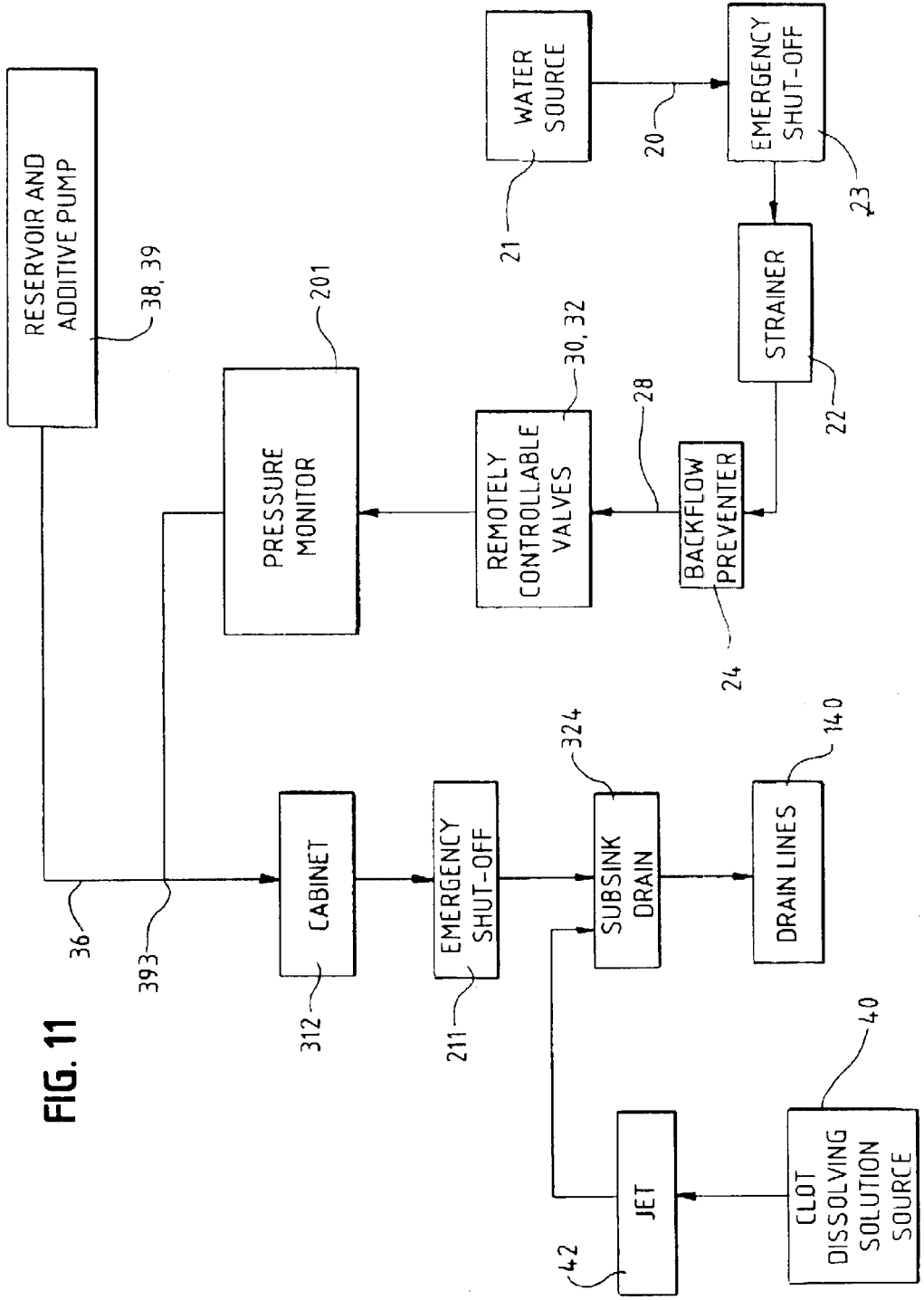
FIG. 11 is a schematic diagram of the plumbing system for the system of FIG. 1.

The plumbing system of FIG. 1 is illustrated schematically in FIG. 11. The plumbing system generally includes a water inlet line 20 connected to a suitable pressurized water source 21, such as the normal municipal water service, a water tank or a water pump. A strainer 22 is provided in the water inlet line 20 and a backflow preventer valve 24 is provided downstream therefrom.

The water supply 28 includes a gate-type shut-off valve 30 and a solenoid-actuated valve 32 in line therewith. The water inlet line 20 ultimately communicates with junction 393 that communicates via cleaning solution injection lines 36 with an additive pump and reservoir 38, 39 that are housed within cabinet 312. The reservoir preferably contains a cleaning solution for killing virus and bacteria (for example bleach) and a suitable defoamer. Activation of the pump causes the additives from the reservoir to mix with the water in the plumbing system so that a pressurized and diluted cleaning solution is emitted by the spray system in the cabinet.

An optional clot-dissolving solution source 40 communicates with a jet 42 directed into the subsink drain 324 and functions to dissolve blood clots in the drain.

A pressure flow sensor 201 monitors the flow of the solution into the cabinet. As described in commonly-assigned U.S. Pat. No. 5,901,717, a microprocessor may control valves 32 and the pump 39 to achieve the desired additive concentration. A remotely controlled emergency shut-off 211 allows the microprocessor to shut off the drain 324 as well as all fluid inputs in the event that monitored parameters are outside of predetermined limits. Additionally, a water flow sensor and a water temperature sensor maybe added to monitor the system.

It is to be understood that while certain forms of the present invention have been illustrated and described herein, it is not to be limited to the specific forms or arrangement of parts described and shown.

What is claimed is:

1. A canister for use in a liquid waste disposal device featuring a lid removal bracket and a canister bracket, said canister comprising:
    a) a lid including a patient port, a vacuum port and a lip adapted to be engaged by the lid removal bracket of the liquid waste disposal device;
    b) a body including an open top surrounded by a circumferential rim, said circumferential rim engaged by the lid in a removable fashion; and
    c) a tab attached to an exterior surface of the body of the canister in a generally horizontal extending fashion, said tab sized and vertically spaced from said circumferential rim so as to engage the canister bracket of the liquid waste disposal device when the canister body is positioned therein and turned about a generally vertical axis.

2. The canister of claim 1 wherein the lip of the lid surrounds a remaining portion of the lid in a circumferential fashion and has a diameter larger than a diameter of the circumferential rim of the body of the canister.

3. The canister of claim 1 wherein the lip of the lid includes a generally horizontal lid removal tab adapted to be engaged by the lid removal bracket of the liquid waste disposal device when the canister body is placed in the canister bracket and turned about a generally vertical axis.

4. The canister of claim 1 wherein the lid engages the circumferential rim of the canister in a press-fit fashion.

5. The canister of claim 1 wherein said body is constructed from polycarbonate plastic.

6. The canister of claim 1 wherein the lid is molded from polystyrene plastic.

* * * * *